(12) United States Patent
Scott et al.

(10) Patent No.: US 7,345,222 B1
(45) Date of Patent: Mar. 18, 2008

(54) USE OF DNA SEQUENCES FOR MALE STERILITY IN TRANSGENIC PLANTS

(75) Inventors: Roderick John Scott, Bath (GB); Wyatt Paul, Cambridge (GB); Pascual Perez, Chanonat (FR)

(73) Assignee: Gene Shears Pty. Limited, Canberra (AU)

( * ) Notice: Subject to any disclaimer, the term of this patent is extended or adjusted under 35 U.S.C. 154(b) by 0 days.

(21) Appl. No.: 09/169,615

(22) Filed: Oct. 9, 1998

Related U.S. Application Data

(63) Continuation of application No. PCT/GB97/00992, filed on Apr. 10, 1997.

(30) Foreign Application Priority Data

Apr. 11, 1996 (GB) .................................. 9607517

(51) Int. Cl.
C12N 15/82 (2006.01)
C12N 5/04 (2006.01)
A01H 5/00 (2006.01)
A01H 5/10 (2006.01)
A01H 1/02 (2006.01)
C12N 15/29 (2006.01)
C12N 15/56 (2006.01)

(52) U.S. Cl. ...................... 800/303; 800/274; 800/278; 800/287; 800/317.4; 435/200; 435/411; 435/419; 435/468

(58) Field of Classification Search ................ 800/274, 800/278, 287, 303, 317.4; 435/200, 209, 435/411, 468
See application file for complete search history.

(56) References Cited

U.S. PATENT DOCUMENTS

| 5,847,258 A * | 12/1998 | Ryals et al. .................. 800/301 |
| 5,955,653 A * | 9/1999 | Scott et al. .................. 800/303 |
| 6,077,991 A * | 6/2000 | Poovaiah et al. ........... 800/278 |

FOREIGN PATENT DOCUMENTS

| EP | 0116718 | 8/1984 |
| EP | 0198288 | 10/1986 |
| EP | 0270822 | 6/1988 |
| EP | 0329308 | 8/1989 |
| EP | 0344029 | 11/1989 |
| EP | 0392225 | 10/1990 |
| EP | 0412911 | 2/1991 |
| WO | 9211379 | 7/1992 |
| WO | 9302197 | 2/1993 |
| WO | 9738116 | 10/1997 |

OTHER PUBLICATIONS

Payne et al. Accession No. AAV81609 (Feb. 25, 1999).*
Wohlleben, et al., Gene (1998) 70, pp. 25-37.
Becker, et al., Plant Molecular Biology (1992) 20, pp. 1195-1197.
Firek, et al., Plant Molecular Biology (1993) 22, pp. 129-142.
Finnegan, et al., Plant Molecular Biology (1993) 22, pp. 625-633.
Haseloff, et al., Nature (1998) 334, pp. 585-591.
Paul, et al., Plant Molecular Biology (1992) 19, pp. 611-622.
Schmulling, et al., Mol. Gen. Genet. (1993) 237, pp. 385-394.
Worrall, et al., The Plant Cell (1992) 4, pp. 759-771.
An, Plant Physiology (1986) 81, pp. 86-91.
Bevan, Nucleic Acids Research (1984) 12, pp. 8711-8721.
Huttner, et al., Journal of Cellular Biochemistry Supplement (1995) 19A, pp. 220.
Neuhaus, et al., Plant Molecular Biology (1992) 19, pp. 803-813.
Muschietti, et al., The Plant Journal (1994) 6(3), pp. 321-338.

* cited by examiner

*Primary Examiner*—David T Fox
(74) *Attorney, Agent, or Firm*—John P. White; Cooper & Dunham LLP

(57) ABSTRACT

The use of DNA sequences comprising a glucanase coding region operably linked to a promoter, or other regulatory sequence, which provides for expression of the DNA sequence with appropriate tissue and/or temporal specificity, in the preparation of a male sterile transgenic tomato plant is disclosed. In preferred embodiments the promoter is a tapetum specific promoter, eg an A3 or an A9 promoter. DNA sequences comprising the PR-Glucanase coding region and an A3 or an A9 promoter, preferably an A9 promoter are also described, as are transgenic tomato plants, plant cells, propagating material, seeds, antisense DNA sequences and ribozyme encoding DNA sequences for restoration of male-fertility.

14 Claims, 13 Drawing Sheets

Figure 2:
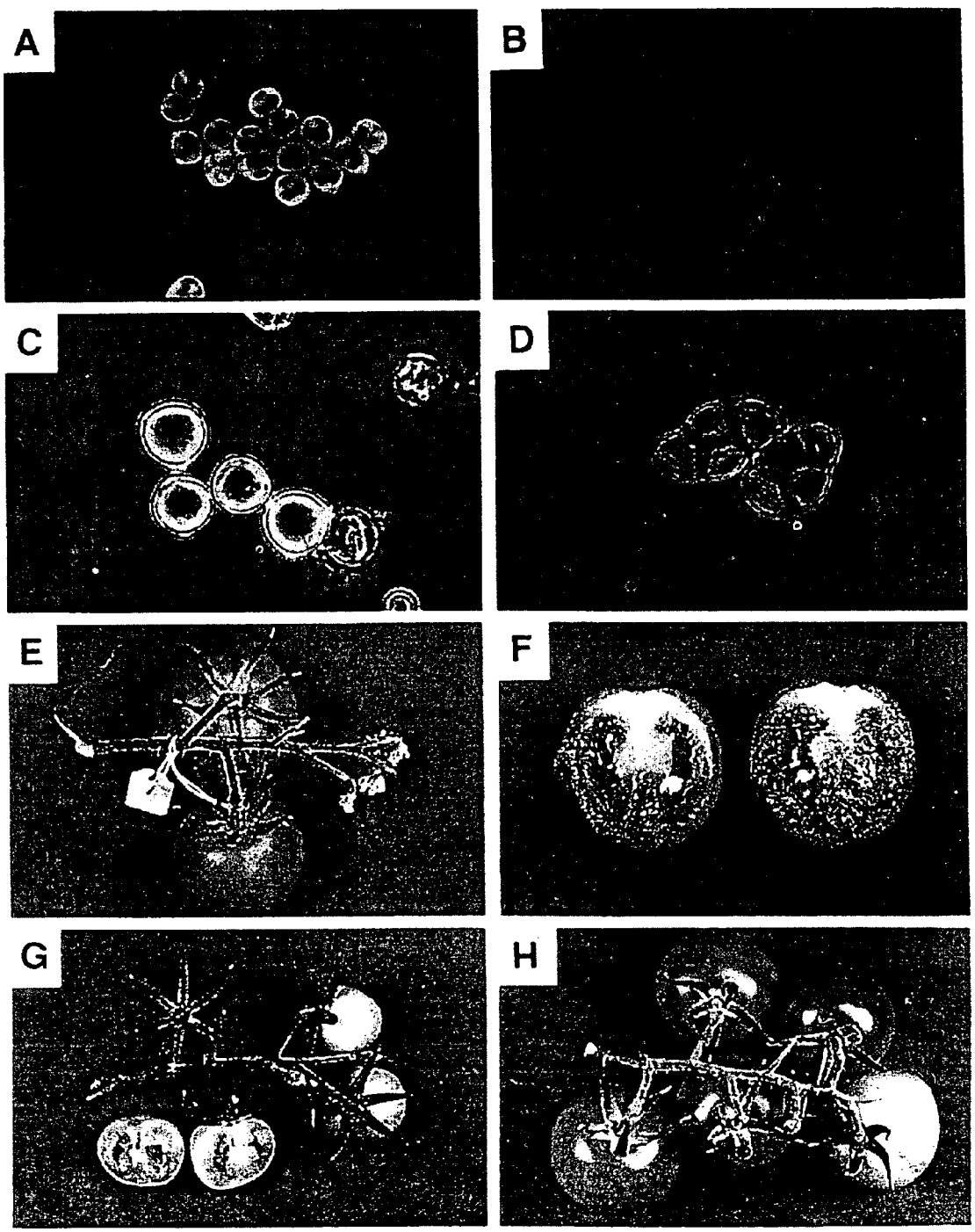

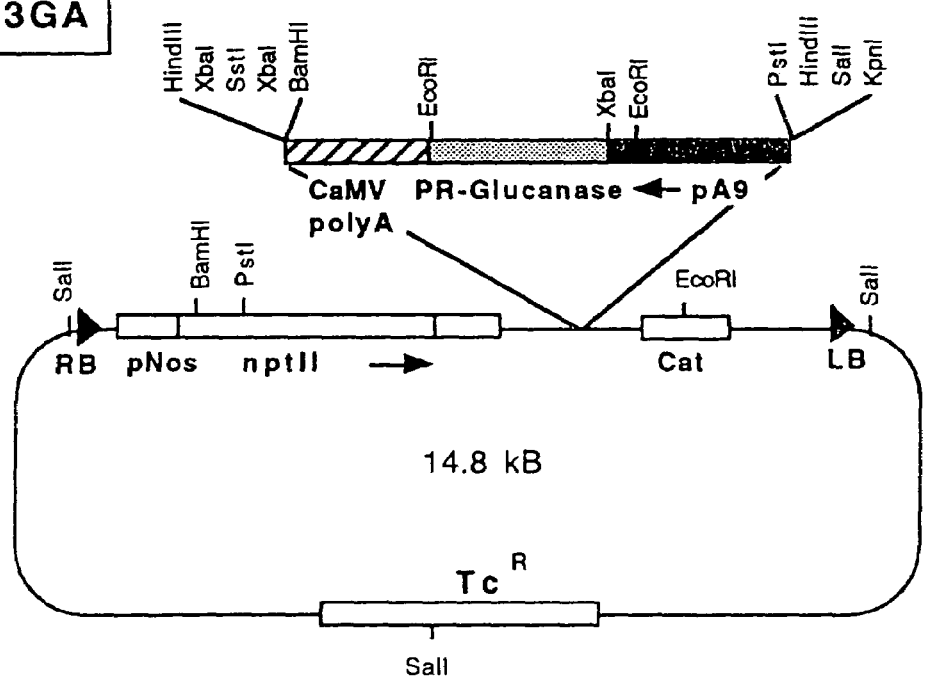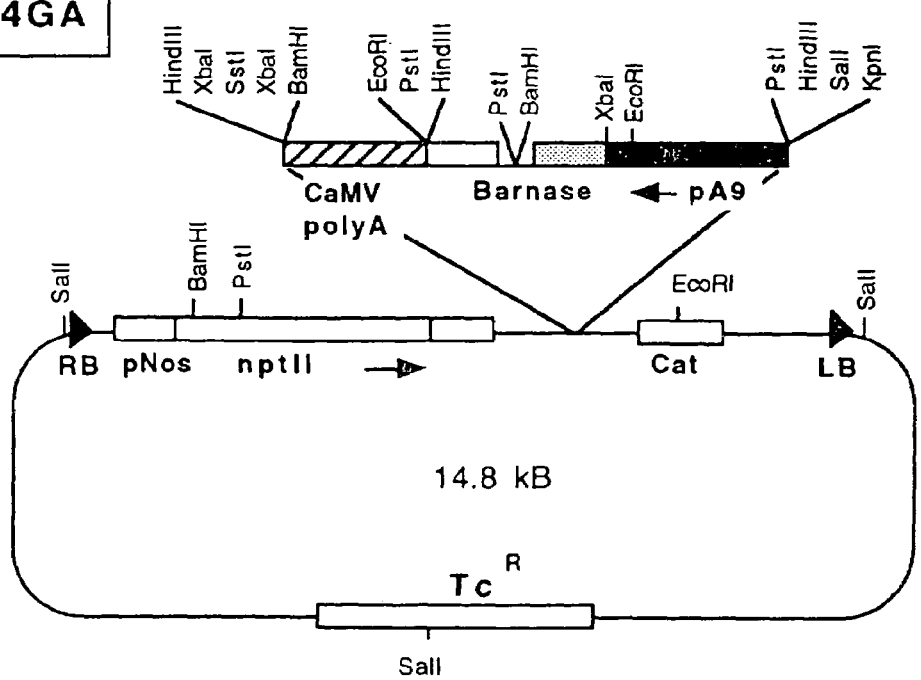
FIG. 1

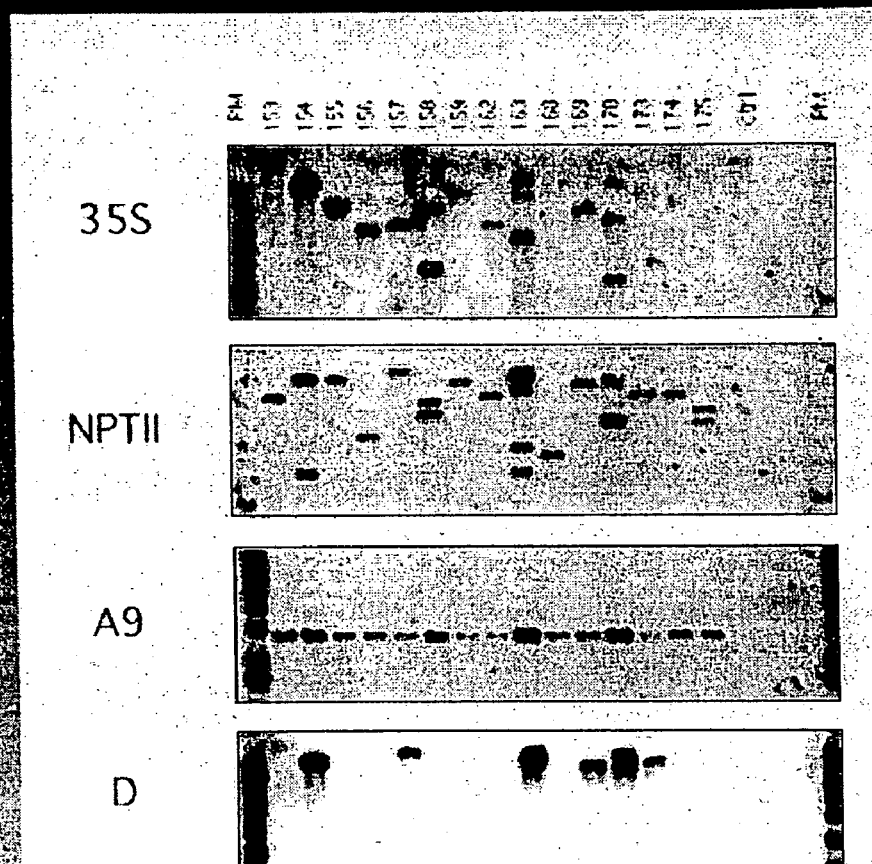
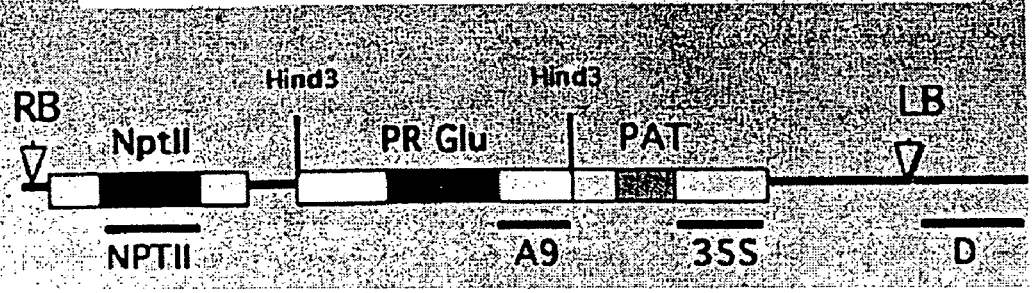
FIG. 4

```
                M  A  A  I  T  L  L  G  L  L  L  V  A  S  S  I  D
TCTAGACCATGGCTGCTATCACACTCCTAGGATTACTACTTGTTGCCAGCAGCATTGACA            60

I  A  G  A  Q  S  I  G  V  C  Y  G  M  L  G  N  N  L  P  N
TAGCAGGGGCTCAATCGATAGGTGTTTGCTATGGAATGCTAGGCAACAACTTGCCAAATC           120

H  W  E  V  I  Q  L  Y  K  S  R  N  I  G  R  L  R  L  Y  D
ATTGGGAAGTTATACAGCTCTACAAGTCAAGAAACATAGGAAGACTGAGGCTTTATGATC           180
                   Site 1

P  N  H  G  A  L  Q  A  L  K  G  S  N  I  E  V  M  L  G  L
CAAATCATGGAGCTTTACAAGCATTAAAAGGCTCAAATATTGAAGTTATGTTAGGACTTC           240

P  N  S  D  V  K  H  I  A  S  G  M  E  H  A  R  W  W  V  Q
CCAATTCAGATGTGAAGCACATTGCTTCCGGAATGGAACATGCAAGATGGTGGGTACAGA           300

K  N  V  K  D  F  W  P  D  V  K  I  K  Y  I  A  V  G  N  E
AAAATGTTAAAGATTTCTGGCCAGATGTTAAGATTAAGTATATTGCTGTTGGGAATGAAA           360

I  S  P  V  T  G  T  S  Y  L  T  S  F  L  T  P  A  M  V  N
TCAGCCCTGTCACTGGCACATCTTACCTAACCTCATTTCTTACTCCTGCTATGGTAAATA           420
        Site 2                      Site 3

I  Y  K  A  I  G  E  A  G  L  G  N  N  I  K  V  S  T  S  V
TTTACAAAGCAATTGGTGAAGCTGGTTTGGGAAACAACATCAAGGTCTCAACTTCTGTAG           480

D  M  T  L  I  G  S  S  Y  P  P  S  Q  G  S  F  R  N  D  A
ACATGACCTTGATTGGAAGCTCTTATCCACCATCACAGGGTTCGTTTAGGAACGATGCTA           540

R  W  F  V  D  P  I  V  G  F  L  R  D  T  R  A  P  L  L  V
GGTGGTTTGTTGATCCCATTGTTGGCTTCTTAAGGGACACACGTGCACCTTTACTCGTTA           600

N  I  Y  P  Y  F  S  Y  S  G  N  P  G  Q  I  S  L  P  Y  S
ACATTTACCCCTATTTCAGTTATTCTGGTAATCCAGGCCAGATTTCTCTCCCCTATTCTC           660

L  F  T  A  P  N  V  V  V  Q  D  G  S  R  Q  Y  R  N  L  F
TTTTTACAGCACCAAATGTGGTGGTACAAGATGGTTCCCGCCAATATAGGAACTTATTTG           720

D  A  M  L  D  S  V  Y  A  A  L  E  R  S  G  G  A  S  V  G
ATGCAATGCTGGATTCTGTGTATGCTGCCCTCGAGCGATCAGGAGGGGCATCTGTAGGGA           780

I  V  V  S  E  S  G  W  P  S  A  G  A  F  G  A  T  Y  D  N
TTGTTGTGTCCGAGAGTGGCTGGCCATCTGCTGGTGCATTTGGAGCCACATATGACAATG           840
    Site 4

A  A  T  Y  L  R  N  L  V  Q  H  A  K  E  G  S  P  R  K  P
CAGCAACTTACTTGAGGAACTTAGTTCAACACGCTAAAGAGGGTAGCCCAAGAAAGCCTG           900

G  P  I  E  T  Y  I  F  A  M  F  D  E  N  N  K  N  P  E  L
GACCTATTGAGACCTATATATTTGCCATGTTTGATGAGAACAACAAGAACCCTGAACTGG           960

E  K  H  F  G  L  F  S  P  N  K  Q  L  K  Y  N  I  N  F  G
AGAAACATTTTGGATTGTTTTCCCCCAACAAGCAGCTCAAATATAATATCAACTTTGGGT          1020

*
GACCGCGG    1028          FIG. 5
```

```
GGAATTCGCCACTCTCGCTGATGAGTCCGTGaGGACGAAAACAACAATCGATGCAGGAG      60
             <------- Ribozyme 4 -------<
TAACTGATGAGTCCGTGAGGACGAAAAATGAGGTTTCTAGAGCATGTGCCAGTCTGATGA    120
------- Ribozyme 3 -------->        <--------
GTCCGTGAGGACGAAACAGGGCTGAATATTATGTTTCTTCTGATGAGTCCGTGAGGACGA    180
<-------- Ribozyme 2 -------->        <------ Ribozyme 1 ------
AACTGTAGAGGATCCAT                                                198
-------->
```

FIG. 9

SEQUENCE LISTING

<160> NUMBER OF SEQ ID NOS: 8

<210> SEQ ID NO 1
<211> LENGTH: 1029
<212> TYPE: DNA
<213> ORGANISM: Brassica sp.

<400> SEQUENCE: 1

```
tctagaccat ggctgctatc acactcctag gattactact tgttgccagc agcattgaca        60
tagcaggggc tcaatcgata ggtgtttgct atggaatgct aaggcaacaa cttgccaaat       120
```

-continued

```
cattgggaag ttatacagct ctacaagtca agaaacatag gaagactgag gctttatgat    180
ccaaatcatg gagctttaca agcattaaaa ggctcaaata ttgaagttat gttaggactt    240
cccaattcag atgtgaagca cattgcttcc ggaatggaac atgcaagatg gtgggtacag    300
aaaaatgtta aagatttctg gccagatgtt aagattaagt atattgctgt tgggaatgaa    360
atcagccctg tcactggcac atcttaccta acctcatttc ttactcctgc tatggtaaat    420
atttacaaag caattggtga agctggtttg ggaaacaaca tcaaggtctc aacttctgta    480
gacatgacct tgattggaag ctcttatcca ccatcacagg gttcgtttag gaacgatgct    540
aggtggtttg ttgatcccat tgttggcttc ttaagggaca cacgtgcacc tttactcgtt    600
aacatttacc cctatttcag ttattctggt aatccaggcc acatttctct ccctattct     660 cttttacag caccaaatgt ggtggtacaa gatggttccc gccaatatag gaacttattt    720
gatgcaatgc tggattctgt gtatgctgcc ctcgagcgat caggaggggc atctgtaggg    780
attgttgtgt ccgagagtgg ctggccatct gctggtgcat tggagccac atatgacaat     840 gcagcaactt acttgaggaa cttagttcaa cacgctaaag agggtagccc aagaaagcct    900
ggacctattg agacctatat atttgccatg tttgatgaga caacaagaa ccctgaactg     960 gagaaacatt ttggattgtt ttcccccaac aagcagctca aatataatat caactttggg   1020
tgaccgcgg                                                           1029
```

<210> SEQ ID NO 2
<211> LENGTH: 337
<212> TYPE: PRT
<213> ORGANISM: Brassica sp.

<400> SEQUENCE: 2

```
Met Ala Ala Ile Thr Leu Leu Gly Leu Leu Leu Val Ala Ser Ser Ile
1               5                   10                  15

Asp Ile Ala Gly Ala Gln Ser Ile Gly Val Cys Tyr Gly Met Leu Gly
                20                  25                  30

Asn Asn Leu Pro Asn His Trp Glu Val Ile Gln Leu Tyr Lys Ser Arg
            35                  40                  45

Asn Ile Gly Arg Leu Arg Leu Tyr Asp Pro Asn His Gly Ala Leu Gln
        50                  55                  60

Ala Leu Lys Gly Ser Asn Ile Glu Val Met Leu Gly Leu Pro Asn Ser
65                  70                  75                  80

Asp Val Lys His Ile Ala Ser Gly Met Glu His Ala Arg Trp Trp Val
                85                  90                  95

Gln Lys Asn Val Lys Asp Phe Trp Pro Asp Val Lys Ile Lys Tyr Ile
            100                 105                 110

Ala Val Gly Asn Glu Ile Ser Pro Val Thr Gly Thr Ser Tyr Leu Thr
        115                 120                 125

Ser Phe Leu Thr Pro Ala Met Val Asn Ile Tyr Lys Ala Ile Gly Glu
    130                 135                 140

Ala Gly Leu Gly Asn Asn Ile Lys Val Ser Thr Ser Val Asp Met Thr
145                 150                 155                 160

Leu Ile Gly Ser Ser Tyr Pro Pro Ser Gln Gly Ser Phe Arg Asn Asp
                165                 170                 175

Ala Arg Trp Phe Val Asp Pro Ile Val Gly Phe Leu Arg Asp Thr Arg
            180                 185                 190

Ala Pro Leu Leu Val Asn Ile Tyr Pro Tyr Phe Ser Tyr Ser Gly Asn
        195                 200                 205
```

```
Pro Gly Gln Ile Ser Leu Pro Tyr Ser Leu Phe Thr Ala Pro Asn Val
    210                 215                 220

Val Val Gln Asp Gly Ser Arg Gln Tyr Arg Asn Leu Phe Asp Ala Met
225                 230                 235                 240

Leu Asp Ser Val Tyr Ala Ala Leu Glu Arg Ser Gly Gly Ala Ser Val
                245                 250                 255

Gly Ile Val Val Ser Glu Ser Gly Trp Pro Ser Ala Gly Ala Phe Gly
                260                 265                 270

Ala Thr Tyr Asp Asn Ala Ala Thr Tyr Leu Arg Asn Leu Val Gln His
            275                 280                 285

Ala Lys Glu Gly Ser Pro Arg Lys Pro Gly Pro Ile Glu Thr Tyr Ile
    290                 295                 300

Phe Ala Met Phe Asp Glu Asn Asn Lys Asn Pro Glu Leu Glu Lys His
305                 310                 315                 320

Phe Gly Leu Phe Ser Pro Asn Lys Gln Leu Lys Tyr Asn Ile Asn Phe
                325                 330                 335

Gly
```

<210> SEQ ID NO 3
<211> LENGTH: 198
<212> TYPE: DNA
<213> ORGANISM: Artificial Sequence
<220> FEATURE:
<223> OTHER INFORMATION: Ribozyme derived from a tomato plant

<400> SEQUENCE: 3

```
ggaattcgcc actctcgctg atgagtccgt gaggacgaaa cacaacaatc gatgcaggag    60
taactgatga gtccgtgagg acgaaaaatg aggtttctag agcatgtgcc agtctgatga   120
gtccgtgagg acgaaacagg gctgaatatt atgtttcttc tgatgagtcc gtgaggacga   180
aacttgtaga ggatccat                                                 198
```

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4

```
tctagaccat ggctgctatc acactcctag g                                   31
```

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5

```
ggaacatgca agatggtggg                                                20
```

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6

```
ccctgtgatg gtggataaga gc                                             22
```

```
<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ggcagcatac acagaatcca gc                                              22

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
ccgcggtcac ccaaagttga tattatattt ga                                   32
```

USE OF DNA SEQUENCES FOR MALE STERILITY IN TRANSGENIC PLANTS

This application is a continuation of PCT International Application No. PCT/GB97/00992, filed Apr. 10, 1997, claiming priority of Great Britain Patent Application No. 9607517.1, filed Apr. 11, 1996, the contents of which are hereby incorporated by reference.

The present invention relates to the use of DNA sequences comprising the coding sequence for a Glucanase enzyme, particularly PR-Glucanase, operably linked to a promoter having an appropriate temporal and/or tissue expression pattern, for instance a tapetum specific promoter, eg an A3 or A9 promoter to transform tomato plants or plant cells to generate male-sterile tomato plants. Tomato plants, and seeds thereof, also form part of the invention.

Hybrid plants have the advantages of higher yield and better disease resistance than their parents, because of heterosis or hybrid vigour. Crop uniformity is another advantage of hybrid plants when the parents are extensively homozygous; this leads to improved crop management. Hybrid seed is therefore commercially important and sells at a premium price.

To date there have been various proposals relating to the production of male-sterile plants. EP-A-0329308 describes various methods for producing male-sterile plants including the use of DNA sequences which code for "antisense" RNA which can block expression of one or more genes essential for pollen production as well as the use of a pollen specific promoter to drive expression of a DNA sequence coding for a cytotoxic molecule.

EP-A-0344029 similarly describes methods for producing male-sterile plants which are based on the use of "antisense" DNA sequences as well as the use of tissue specific promoters to control expression of a cytotoxic molecule. Examples of such cytotoxic molecules provided in EP-A-0344029 are RNase T1, Barnase, DNases, proteases, phytohormones, enzymes involved in the synthesis of auxin, glucanases, lipases, lipid peroxidases, plant cell wall inhibitors and bacterial toxins.

Methods which rely on the expression of a cytotoxic substance in particular tissues are, of course, dependent upon the availability of tissue specific promoters. WO-A-92/11379 provides certain Tapetum-specific promoters, designated A3 and A9 which are useful in methods for the production of male-sterile plants by means of tissue and temporal specific expression of a cytotoxic substance.

Barnase in particular has been put forward as a particularly useful cytotoxic molecule for use in producing male-sterile plants. However, Barnase does not appear to be useful in all plant species. In particular it has now been found to have certain side effects in Tomato plants which have been transformed with a DNA molecule comprising a Barnase coding sequence under the control of a tissue specific promoter. Thus, at present there is no useful method for the production of male-sterile Tomato plants.

Surprisingly, we have now found that in the case of tomato plants the use of, for example, a tapetum specific promoter to drive expression of a DNA sequence encoding a glucanase enzyme does represent a particularly effective method of producing male-sterile tomato plants which avoids the side effect problems experienced with Barnase. Examples of useful tapetum specific promoters include the A3 or A9 promoters described in WO-A-92/11379.

Thus, in a first aspect, the present invention provides the use of:
(i) a DNA sequence comprising the coding sequence of a glucanase enzyme;
(ii) a DNA sequence substantially homologous to a DNA sequence as defined in (i); or
(iii) a DNA sequence coding for a protein substantially homologous to the glucanase as defined in (i) or (ii);

operably linked to a promoter, or other regulatory sequence, which provides expression of the DNA sequence with appropriate tissue and/or temporal specificity, in the preparation of a male sterile transgenic tomato plant.

In the context of the present invention, "appropriate tissue and/or temporal specificity" means that the promoter provides for expression of the glucanase in such a way that male sterility results in the transgenic tomato plant. For example, the sequence will be expressed in tissues where its activity will lead to male sterility. Time of expression may also be important and hence the need for a degree of temporal specificity.

Suitably, the DNA sequence will be operably linked to a promoter, or other regulatory sequence, which provides for expression of the DNA sequence in the tapetum and/or microsporogenous cells prior to expression of callase. Thus, tapetum specific promoters with appropriate temporal expression patterns are particularly useful, eg an A3 or an A9 promoter as disclosed in WO-A-92/11379, as well as sequences which consist only of those regulatory elements from such promoters which are required to initiate tissue specific expression.

Additionally, promoters which have desired temporal specificity but which are more generally expressed throughout plant tissue may also be useful in the practice of the present invention, provided that they are active in the appropriate tissues, and hence the use of such promoter sequences are also within the scope of the invention.

In the case of (i) as defined above the coding sequence for the glucanase enzyme will be the natural coding sequence. For sequences as defined in (ii) above, it is a sequence substantially homologous to the natural coding sequence. The skilled man will appreciate that due to the degeneracy of the genetic code it is possible to make conservative changes to the DNA sequence which will not result in changes to the amino acid sequence of the glucanase enzyme. In addition, sequences defined in (iii) above are also within the scope of the invention. It is well known in the protein art that "conservative" or indeed "semi-conservative" changes can be made to the amino acid sequence of a protein which will not alter its fundamental activity. For example, amino acids such as glycine, valine, leucine and isoleucine, which all have aliphatic side chains, may often be substituted for each other without substantially altering the biological activity of the protein. Similarly, amino acids such as phenylalanine, tyrosine and tryptophan, which all have aromatic side chains, may be substituted for each other. Thus, the use of DNA sequences coding for such modified forms of the glucanase enzyme are also within the scope of the present invention.

In the context of (iii) as defined above, the proteins coded for by the DNA sequence which are substantially homologous to the glucanase protein as defined in (i) or (ii) above, may be 40%, 50%, 60%, 70%, 80%, 90%, 95% or even 99% homologous. Preferably, the protein will be 60% homologous, more preferably 80% homologous, even more preferably 90% homologous and most preferably 95% homologous.

In the context of the present invention, the term "promoter, or other regulatory sequence" includes the complete promoter sequence eg the A3 or A9 promoter, or may refer to those elements or parts of the promoter sequence which provide the necessary tissue and/or temporal specificity. Thus, the skilled man would understand that a complete promoter sequence could be so modified to remove non-essential, non-regulatory elements if required. In addition, it would be possible to modify constitutive promoters by inclusion of tissue and/or temporal control sequences from promoters such as the A3 or A9 promoters to produce composite or chimeric promoter sequences useful in the practice of the invention.

As mentioned above, examples of suitable tapetum specific promoters include the A3 and A9 promoters. In addition, it will also be understood by the skilled man that such A3 or A9 promoters can be derived not only from *Brassicaceae* spp as disclosed in WO-A-92/11379, but also from other sources, for instance from Maize. Thus, the use of A3 or A9 "like" promoters derived from such other sources, eg the A9 "like" promoter from Maize also form part of the present invention.

In a preferred embodiment, the promoter will be either the complete A9 promoter or at least those regulatory elements essential for initiation of transcription. In particular the A9 promoter from *Brassicaceae* spp. is preferred. One example of a preferred glucanase enzyme whose DNA coding sequence is useful in the present invention is β(1,3)PR-Glucanase. A DNA sequence encoding this enzyme is shown in FIG. 5.

DNA for use in accordance with the invention may be in the form of a vector. Examples of suitable vectors include plasmids, cosmids, artificial chromosomes, viruses or phages. In addition, DNA sequences used in the invention may include one or more selectable markers to enable selection of cells transfected (or transformed: the terms are used interchangeably in this specification) with them and, preferably, to enable selection of cells harbouring vectors incorporating heterologous DNA. One example of such a selectable marker is a gene which when expressed will confer herbicide resistance, eg a gene conferring resistance against the herbicide BASTA.

Although EP-A-0344029 included glucanases as an example of cytotoxic molecules for use in conferring male sterility, this was disclosed only as part of a general list of possibilities of apparently equal merit, and this disclosure did not include any discussion of the particular problems associated with producing a useable male sterile tomato plant.

WO-A-92/11379 disclosed DNA constructs comprising the A3 or A9 promoter from *Brassicaceae* and the coding sequence for β-1,3 glucanase from *N. tabacum*. However, this disclosure also included examples using the A3 or A9 promoter to drive expression of Barnase, and again no discussion of the particular advantages of using an A3/A9-glucanase system in a tomato plant was disclosed.

DNA for use in accordance with the invention can be prepared by any convenient method involving coupling together successive nucleotides, and/or ligating oligo- and/or poly-nucleotides, including in vitro processes, but recombinant DNA technology forms the method of choice. Ultimately, the DNA will be introduced into plant cells, by any suitable means.

Preferably, plant cells are transformed with DNA using a disarmed Ti-plasmid vector and carried by *Agrobacterium* by procedures known in the art, for example as described in EP-A-0116718 and EP-A-0270822. Alternatively, the foreign DNA could be introduced directly into plant cells using an electrical discharge apparatus. Any other method that provides for the stable incorporation of the DNA within the nuclear DNA of any plant cell of any species would also be suitable.

Although the provision of male-sterile plants is advantageous, there is also a need to provide a means for the restoration of fertility. One may wish to ensure, for instance, that 100% of F1 hybrid plants are fertile. A convenient way to achieve this is by the use of a restorer gene or sequence. In the context of the present invention this restorer gene can comprise DNA encoding RNA which is in the antisense orientation relative to the RNA transcribed from the glucanase DNA sequence. This restorer DNA can be operably linked to a promoter which displays an appropriate temporal and tissue expression pattern, eg that used to drive expression of the glucanase DNA sequence as described above. Thus, promoters, or other regulatory sequences as described herein are equally useful in providing for restoration of male fertility. Thus, it can be operably linked to a tapetum specific promoter such as an A3 or A9 promoter as described herein.

In a second aspect, therefore, the present invention provides the a DNA sequence which is complementary to at least part of a DNA sequence coding for a glucanase as defined in (i), (ii) or (iii) above. Suitably, the DNA sequence of this aspect of the invention is operably linked to a promoter, or other regulatory sequence, which provides for expression of the DNA sequence with appropriate tissue and/or temporal specificity. In preferred embodiments, the promoter, or other regulatory sequence, will be as described above for use with the glucanase encoding DNA sequence.

Suitably, the antisense DNA sequence is complementary to at least a part of the DNA sequence encoding PR-Glucanase, eg is complementary to at least part of the sequence shown in FIG. 5.

A still further example of fertility restorer DNA encodes an RNA enzyme (known as a ribozyme) capable of highly specific cleavage against a given target sequence (Haseloff and Gerlach *Nature* 334 585-591 (1988)). Like antisense DNA, for ribozyme DNA (coding in this instance for a ribozyme which is targeted against the RNA encoded by a glucanase coding sequence) it may be possible to use any appropriate promoter, or other regulatory sequence as described herein to drive ribozyme-encoding DNA.

Thus, according to a third aspect of the invention, there is provided a DNA sequence encoding a ribozyme capable of specific cleavage of RNA encoded by a DNA molecule as defined in (i), (ii) or (iii) as described herein. Suitably, the ribozyme encoding DNA sequence can be under the control of a promoter, or other regulatory sequence, which provides for expression of the ribozyme encoding DNA sequence with appropriate tissue and/or temporal specificity, eg a tapetum specific promoter such as an A3 or an A9 promoter, preferably an A9 promoter. In a preferred embodiment the ribozyme is capable of specifically cleaving RNA derived from a DNA sequence coding for PR-Glucanase. A suitable ribozyme coding DNA sequence is shown in FIG. 9.

The present invention contemplates the use of all forms of ribozyme. These include ribozymes as described by Haseloff and Gerlach (*Nature,* 334:585-591 (1988)), ribozymes which form part of an expressed message, ribozymes which are embedded within snRNA or tRNA and multimeric ribozymes, which in turn can be comprised of the same or different individual ribozymes.

Both the complementary DNA sequences of the invention as well as the ribozyme-encoding DNA of the invention would be useful in restoring male fertility in tomato plants. Thus, in a fourth aspect, the present invention provides the use of such DNA sequences of the invention in the restoration of male-fertility in a tomato plant.

Thus, the use of the glucanase encoding DNA sequences as defined herein enables the production of transgenic tomato plants which are male-sterile. Thus, in a fifth aspect, the present invention provides a transgenic tomato plant which has incorporated in at least some of its cells a glucanase encoding DNA sequence as defined herein and as described above.

In a sixth aspect, the present invention provides a transgenic tomato plant which has incorporated in at least some of its cells a complementary or ribozyme encoding DNA sequence of the invention.

In further aspects the present invention provides:
(i) a plant cell including a glucanase encoding DNA sequence of the invention;
(ii) a plant cell including a complementary or ribozyme encoding DNA sequence of the invention;
(iii) propagating material derived from a transgenic plant of the invention;
(iv) seeds obtainable from a transgenic plant of the invention; and
(v) a method for restoring male fertility in a male-sterile tomato plant which comprises:
  (i) producing a male-sterile transgenic tomato plant of the invention; and
  (ii) crossing the transgenic tomato plant produced in step (i) with a transgenic tomato plant of the invention which has incorporated in at least some of its cells a complementary or ribozyme encoding DNA sequence of the invention.

Preferred features of each aspect of the invention are as for each other aspect mutatis mutandis.

Figure 3:
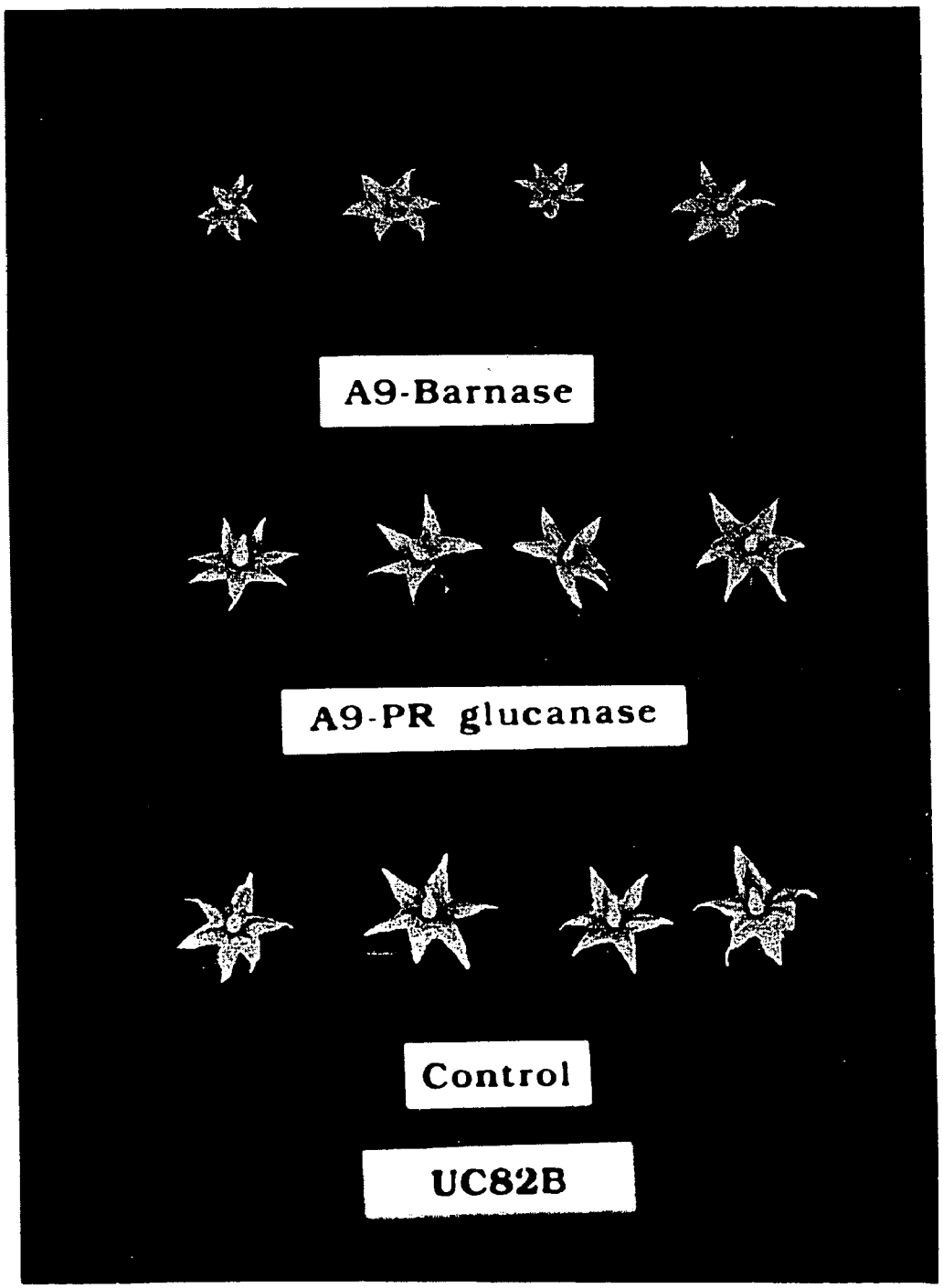
Figure 6:
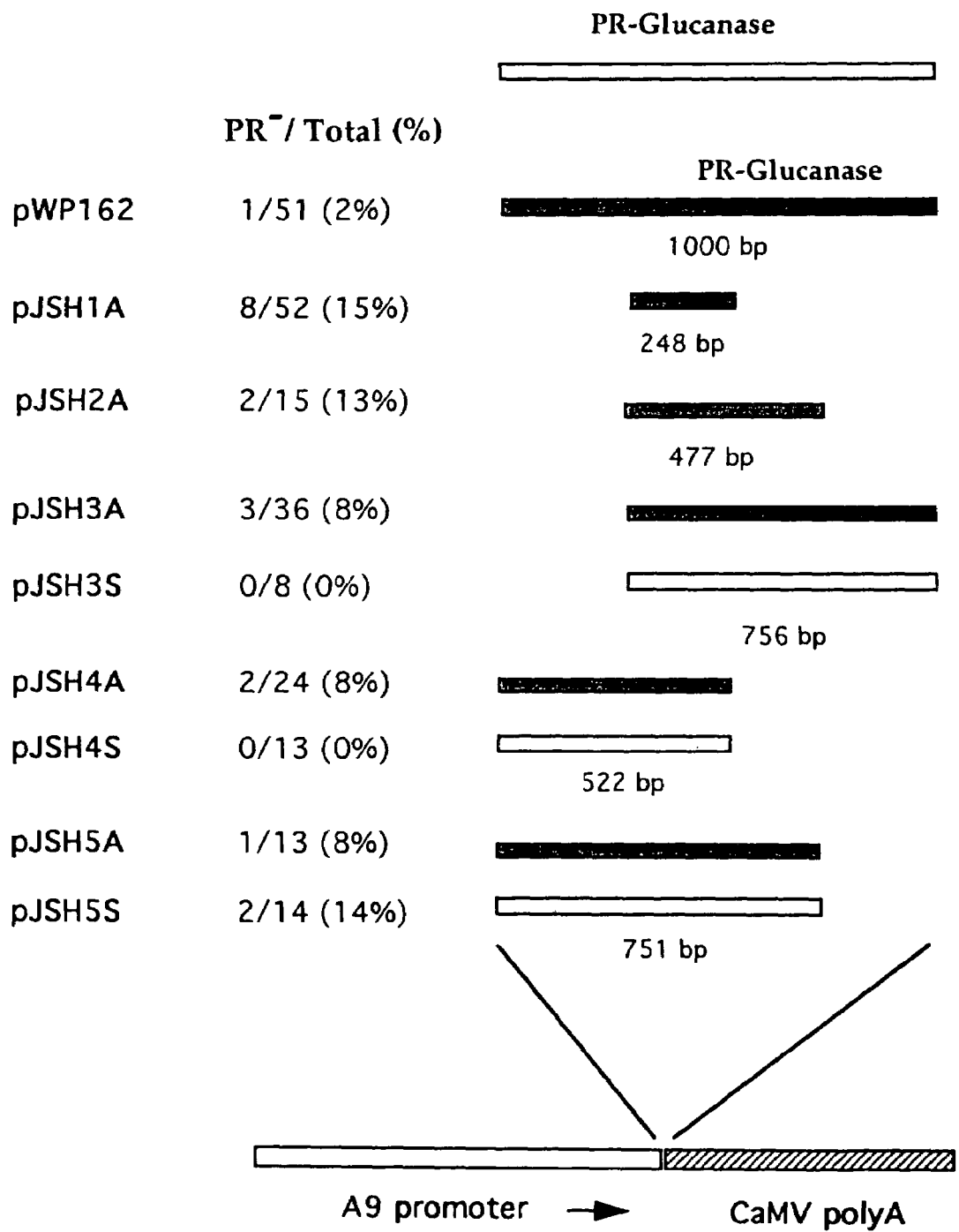
Figure 7:
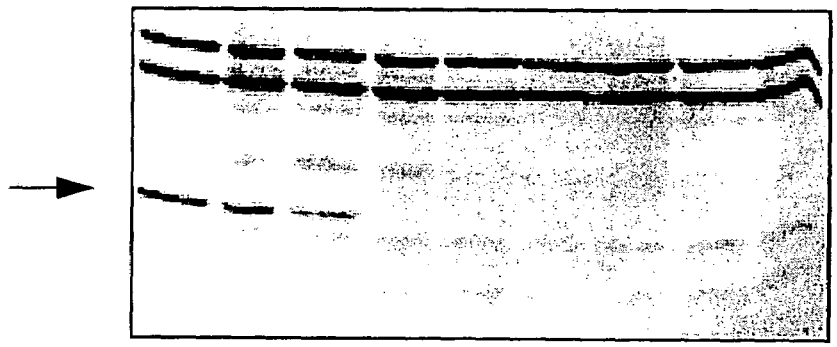
Figure 10:
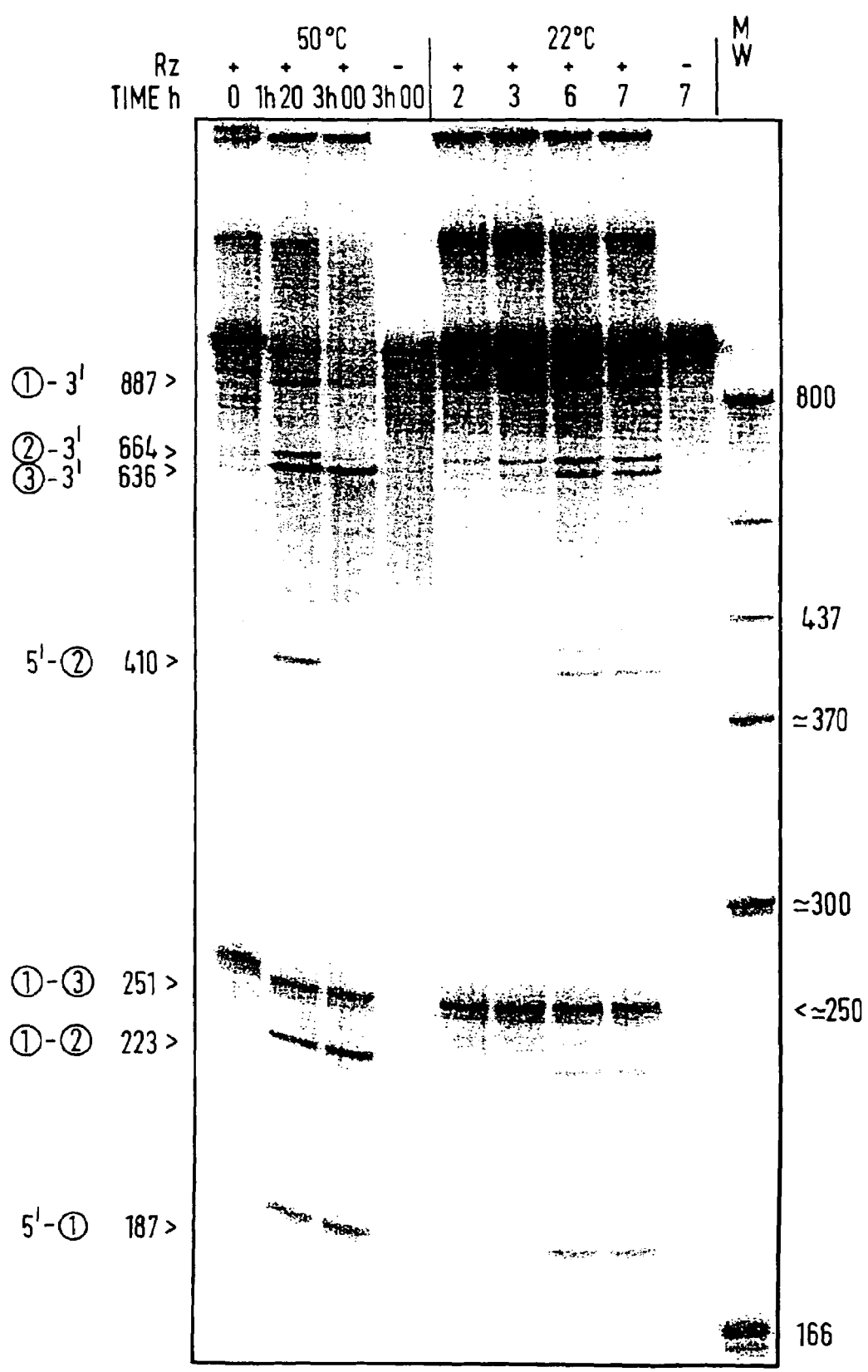
Figure 11A:
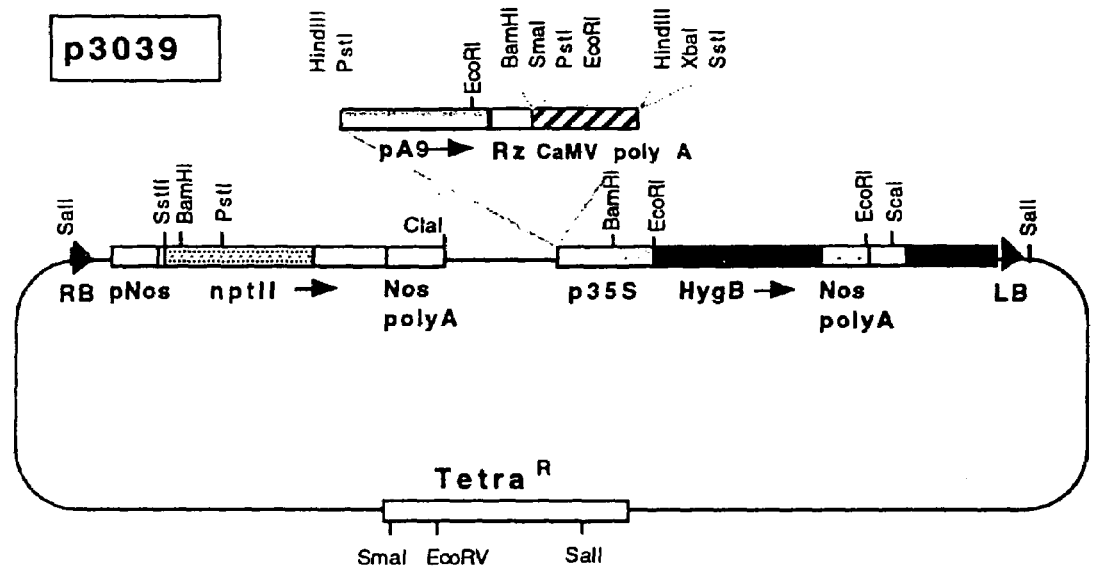
Figure 11B:
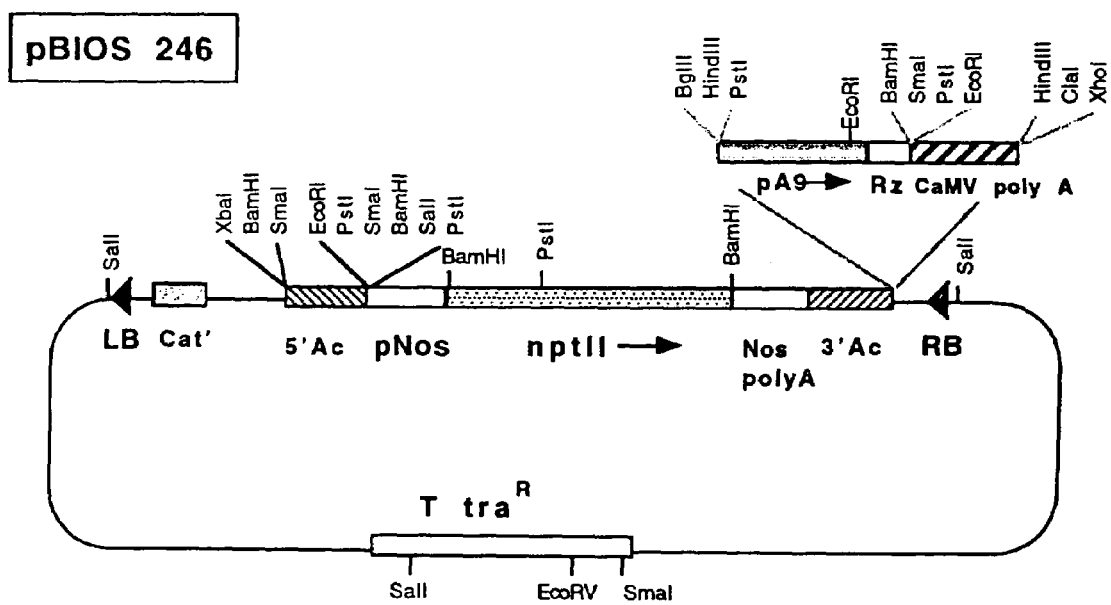
Figure 12:
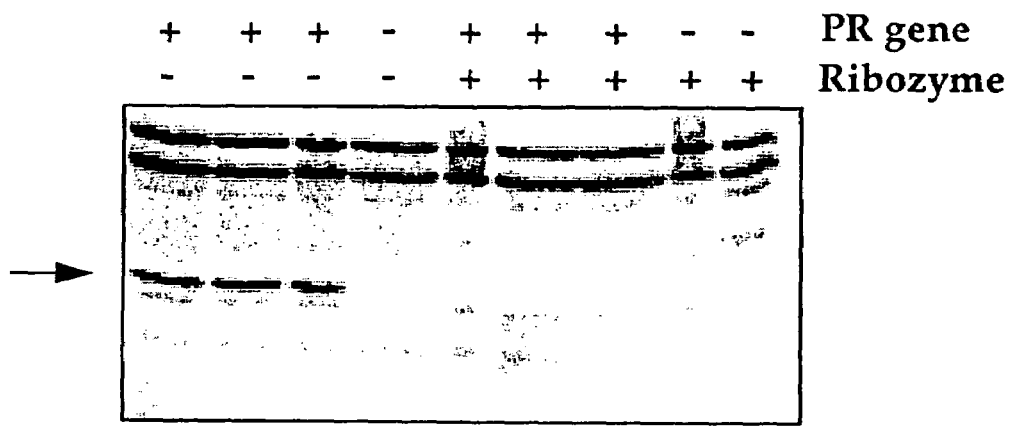

The invention will now be described with reference to the following examples, which should not be construed as in any way limiting the invention. The examples refer to the figures in which:

FIG. 1: is a schematic diagram of plasmids pWP173GA and pWP174GA;

FIG. 2: shows the phenotype of A9-PR-Glucanase (WP173GA) tomato plants: A) Wild-type tetrads stained with Aniline Blue for callose; B) A9-PR Glucanase tetrads stained with Aniline Blue callose surrounding tetrads has been degraded by PR-Glucanase; C) Wild-type mature pollen D) PR-Glucanase plant lacks mature pollen but has tetrad-like fused microspores at anther dehiscence; E) A9-PR-Glucanase plant; the first two flowers on the truss have been cross-pollinated with wild-type pollen; F) Section of cross-pollinated derived fruit from an A9 PR-Glucanase plant hybrid seed can be seen; G) Parthenocarpic fruit on a non-cross pollinated A9 PR Glucanase plant; this fruit has no seed. H) Wild-type segregant from an A9. PR Glucanase plant line; this exhibits normal fruit set;

FIG. 3: shows floral morphology of wild-type tomato plants and male sterile WP173GA and WP174GA plants; the A9-Barnase plants have flowers that are reduced in size compared to wild-type and A9-PR Glucanase plants;

FIG. 4: shows the molecular analysis of 15 transgenic tomatoes carrying A9-PR glucanase and Basta resistance genes;

FIG. 5: shows the sequence of the PR-Glucanase gene (SEQ ID NO. 1) and encoded protein (SEQ ID NO. 2). Regions that are underlined are complementary in sequence to the arms of the ribozymes described in Example 6;

FIG. 6: is a schematic diagram showing the antisense (filled boxes) and partial sense (open boxes) PR-Glucanase fragments cloned behind the A9-promoter; the number and proportion of tobacco retransformants that lacked detectable PR-Glucanase protein, as determined by Western analysis, is indicated;

FIG. 7: shows Western analysis of PR-Glucanase protein levels in anthers (from buds of 8-10 mm in length) of progeny of a male-fertile (restored) tobacco plant transformed with the A9-antisense PR-Glucanase construct, pJSH1A; the genotype of the tobacco plants is indicated above each lane; plants containing the A9—PR Glucanase gene but not the A9-antisense PR-Glucanase gene contain PR-Glucanase protein in anthers (arrowed); plants containing both the A9-PR Glucanase and A9 antisense PR-Glucanase genes lack the PR-Glucanase protein; antibody a gift from Pierre De Wit (raised against tomato acidic β-1,3-glucanase);

FIG. 8: shows schematic diagrams of (A) 35S-Ac plasmid pBIOS144, (B) A9-PR-Glucanase antisense and (C) A9-PR-Glucanase partial sense plasmids used to transform tomato;

FIG. 9: shows the DNA sequence of the multimeric ribizyme (SEQ ID NO. 3); the adenosine residue (lower case) at position 15 of the catalytic unit of ribozyme 4 is missing in the final multimeric ribozyme;

FIG. 10: shows in vitro activity of the multimeric ribozyme at 50° C. and at 22° C.; the sizes and origins of the various cleavage products are indicated to the left of the gel; no cleavage products that result from ribozyme cleavage at site 4 can be seen;

FIG. 11: is a schematic diagram of A9-multimeric ribozyme plasmids used to transform tobacco (A) and tomato (B); and FIG. 12: Western analysis of PR-Glucanase protein levels in anthers (from buds of 8-10 mm in length) of progeny of a male-fertile (restored) tobacco plant transformed with the A9-ribozyme construct, p3039; plants containing both the A9-PR Glucanase and A9 multimeric ribozyme genes lack the PR-Glucanase protein (arrowed).

EXAMPLE 1

Comparison of the Phenotype of A9 Promoter-PR Glucanase Tomato Plants with A9 Promoter Barnase Tomato Plants When transformed into the model plant species tobacco, both the A9 promoter—Barnase and A9 promoter-PR glucanase chimaeric genes will cause male sterility (Paul et al, *Plant Molecular Biology*, 19:611-622 (1992); Worrall et al, *Plant Cell*, 4:759-771 (1992)). In the case of A9-Barnase, the majority of the male sterile plants were phenotypically normal. To determine which AMS gene is superior in the closely related species tomato, both AMS genes were transferred into a binary vector that is preferred for tomato transformation. This binary vector, pGA492 (An, *Plant Physiology*, 81:86-91 (1986)), gives a higher number of tomato transformants than the vector pBin19 (Bevan et al, *Nucl. Acids Res.*, 12:8711-8721 (1984)) which was used in previous experiments in tobacco.

First the KpnI, EcoRV A9-PR Glucanase chimaeric gene fragment of pDW80PR (Worrall et al (1992) supra) was cloned between the KpnI and SmaI sites of pBluescript KS+ (Stratagene) forming pWP173. Secondly the A9-PR Glucanase gene of pWP173 was transferred as a KpnI, SstI fragment into KpnI, SstI-cut pGA492 forming pWP173GA (FIG. 1).

Similarly the KpnI, EcoRV A9-Barnase chimaeric gene fragment of pWP127 (Paul et al (1992) supra) was cloned between the KpnI and SmaI sites of pBluescript KS+ forming pWP174. The A9-Barnase gene was then transferred from pWP174 as a KpnI-SstI fragment into KpnI, SstI-cut pGA492 forming pWP174GA (FIG. 1). Both plasmids were then transferred to *Agrobacteria* which was then used to transform tomato and the primary transformants scored for male fertility.

Of 31 tomato plants transformed with the PR-Glucanase gene, 26 plants exhibited complete male sterility with no observable pleiotropic effects (FIG. 2). Progeny of primary transformants, which contained a single copy of the A9-PR Glucanase gene, were analysed and shown to be completely male sterile if they inherited the A9-PR Glucanase gene.

Of 29 tomato plants transformed with the A9-Barnase gene only 11 exhibited male sterility. However 50 k of the male sterile plants also exhibited additional pleiotropic effects including stunted growth with small and malformed flowers (FIG. 3). These additional phenotypes are likely to be due to inappropriate expression of Barnase, perhaps due to the influence of flanking plant DNA sequences. Although some A9-Barnase plants were male sterile without obvious additional phenotypes there is a possibility that such plants may also inappropriately express Barnase in certain environmental conditions.

Thus the A9-PR-Glucanase gene is preferred for the creation of male sterile tomato plants.

EXAMPLE 2

Linkage of the A9-Glucanase Chimaeric Gene to BASTA Resistance and Field Trials

In dominant male sterility systems the AMS plants are maintained by pollination with wild type plants. Seed produced on the AMS plant will therefore be a 1:1 mixture of AMS and wild-type plants. To select for tomato seedlings that contain the AMS gene, the A9-PR glucanase gene is linked to the herbicide resistance gene phosphinothricin acetyl transferase, PAT (Wohlleben et al, *Gene,* 70:25-37 ('988)) which confers resistance to the herbicide BASTA. A 1.6 kb KpnI fragment encoding the CaMV 35S promoter-PAT chimaeric gene from PBASTA (a derivative of pIB16.1 (Broer et al, In proceedings of the Braunschweig Symposium on Applied Plant Molecular Biology, Braunschweig, November 21-23 (1989) pp 240-246) was cloned into the KpnI site of pWP173GA forming pBIOS171 (FIG. 4). pBIOS171 was transformed into tomato (FIG. 4). Of 21 primary transformants 16 were male sterile. In progeny of plants containing a single copy of the BASTA-A9-PR glucanase gene, BASTA resistance co-segregated with male sterility. A field trial of 4 male sterile lines demonstrated that complete male sterility was maintained over a flowering period of 90 days (at which point the trial was terminated).

EXAMPLE 3

Evaluation of Male Fertility Restoration Genes in Tobacco: A9 Promoter PR-Glucanase Antisense and Partial Sense Chimaeric Genes In order for 100 k of F1 hybrid plants to be male fertile, the male parent used in the hybrid cross must be homozygous for a gene, a restorer gene, that will neutralize the effect of the A9-PR-Glucanase gene. An example of such a restorer gene is an A9-promoter antisense PR-Glucanase gene. The use of the A9 promoter to drive the expression of the restorer gene is preferred, though any promoter having a suitable temporal and/or tissue expression pattern may be equally effective.

Since transformation of tobacco is more efficient than tomato, potential PR-Glucanase restorer genes were evaluated by retransformation of male sterile A9-PR Glucanase tobacco lines described in Worrall et al ((1992) supra). A full-length antisense PR-Glucanase gene was constructed as follows:—The PR-glucanase gene from pDW80PR was recloned as a XbaI, SstII fragment into XbaI, SstII-cut pBluescript SK-forming pWP158. The PR glucanase gene was then recovered from pWP158 as a EcoRI, SstII fragment and cloned between the SstII and EcoRI sites of pWP80 (see WO-A-92/11379) forming pWP162. The A9 driven PR-Glucanase antisense gene was recovered from pWP162 as a SstI, EcoRV fragment and cloned between the SstI and SmaI sites of the binary vector pGPTV-Hpt (Becker et al, *Plant Molecular Biology,* 20: 1195-1197 (199:2)), forming pWP162-Hpt. Of 51 tobacco PR-Glucanase plants transformed with pWP162-hpt 1 appeared to have increased callose levels and almost wild-type pollen production. This plant had 8 copies of the restorer gene.

Further antisense and partial sense PR-Glucanase constructs were constructed in an attempt to improve the frequency of restoration and to obtain plants that were restored to fertility by the presence of a single copy of the restorer gene. Thus the following primers were designed in order to obtain by PCR different fragments of the PR-Glucanase gene:—

```
                                       (SEQ ID NO. 4)
N-term
5' TCTAGACCATGGCTGCTATCACACTCCTAGG 3'
(1-31 bp in FIG. 5)
                                       (SEQ ID NO. 5)
5' GGAACATGCAAGATGGTGGG 3'
PR1 (275-294 bp)
                                       (SEQ ID NO. 6)
5' CCCTGTGATGGTGGATAAGAGC 3'
PRT2 (520-499 bp)
                                       (SEQ ID NO. 7)
5' GGCAGCATACACAGAATCCAGC 3'
PR3 (749-728 bp)
                                       (SEQ ID NO. 8)
5' CCGCGGTCACCCAAAGTTGATATTATATTTGA 3'
(1028-997 bp)
```

Five PCR products were generated and cloned into the vector PGEM-T (Promega), forming plasmids pJSH1 to pJSH5. The PR-glucanase fragments were then cloned in the sense or antisense orientation behind the A9 promoter as outlined in FIG. 6, then transferred into the binary vector pSCV Nos-Hyg (this binary vector is a derivative of pSCV1 (Firek et al, *Plant Molecular Biology,* 22:129-142 (1993)) which contains a nos promoter driving a hygromycin resistance gene, cloned between the EcoRV and EcoRI sites of pSCV1).

The antisense and partial sense constructs were then used to transform a male-sterile tobacco PR-Glucanase line, and the level of PR-Glucanase expression in anthers assessed using an antibody raised against a tomato acidic β-1,3-Glucanase gene. Results shown in FIG. 6 suggest that most of the restorer genes are capable of downregulating expression of PR-Glucanase, the most effective being pJSH1A-SCV with 15% of the retransformed plants lacking detectable PR-Glucanase. These restored plants exhibited normal or near normal male fertility. Analysis of progeny of restored plants containing a single copy of the restorer gene showed that restoration segregated with the restorer gene (FIG. 7) and that the restoration gene was effective in down regulating PR-glucanase expression when transferred into a different A9-PR glucanase line, ie to demonstrate that down regulation by the restorer was only due to the restorer gene, a segregant carrying only the restorer gene was crossed into a different A9-PR glucanase line. Again, the restorer gene was effective in down regulating PR-glucanase expression.

EXAMPLE 4

Figure 8A:
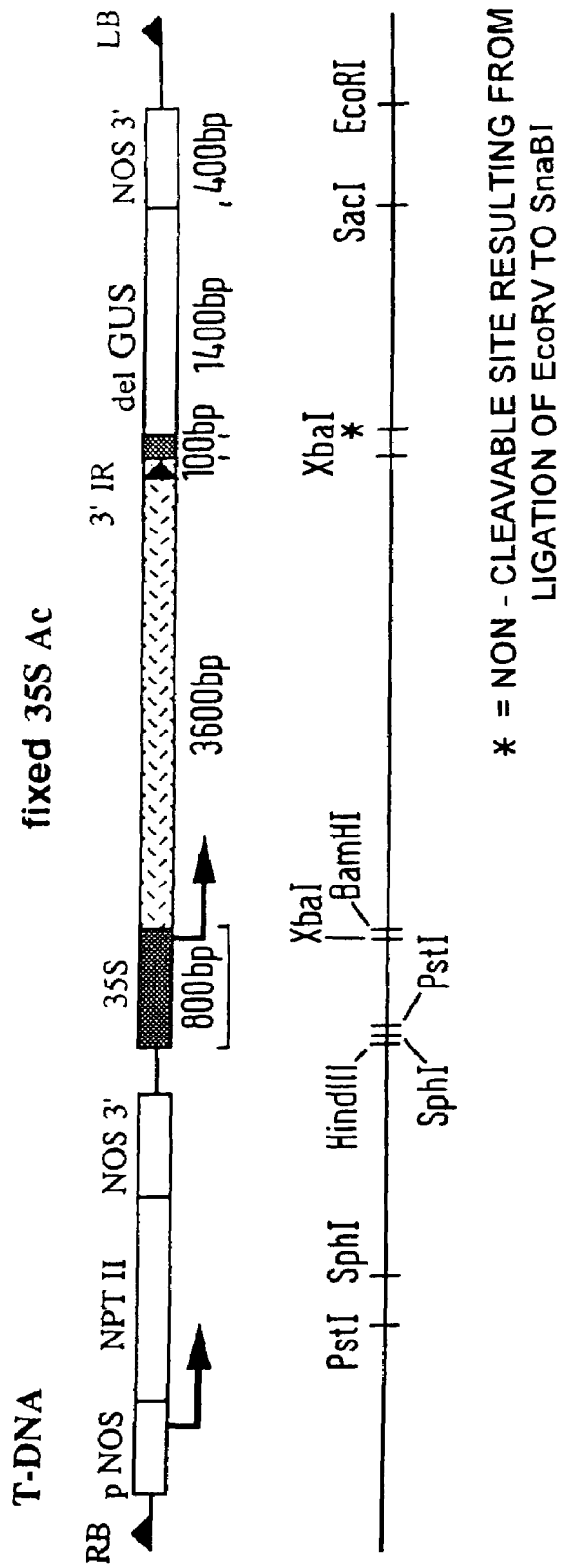
Figure 8B:
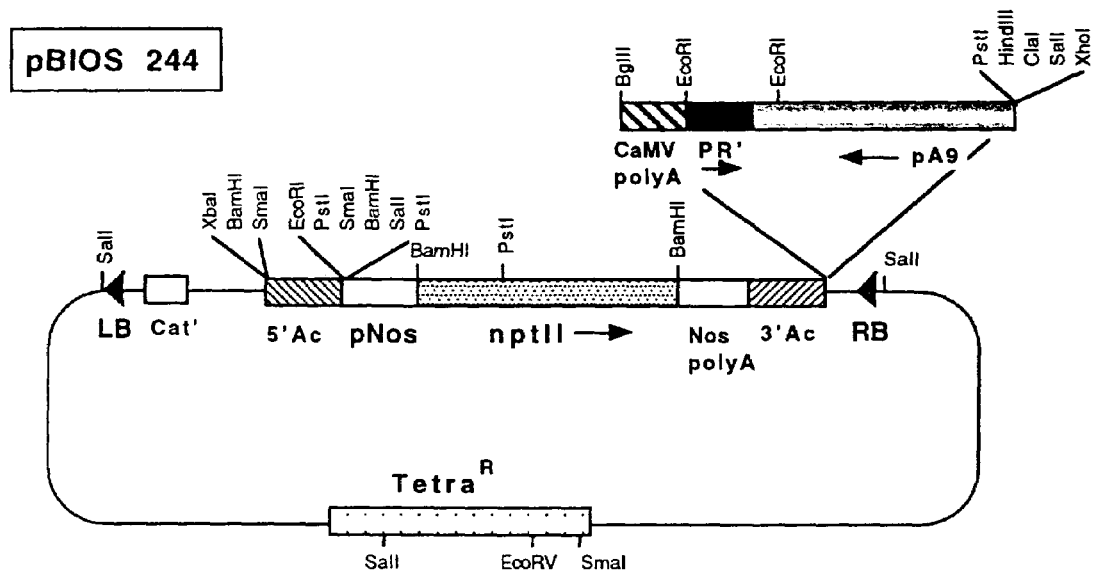

Restoration of Male Fertility in Tomato Plants Containing the A9-PR Glucanase Gene Using Antisense Directed Against PR-Glucanase The most effective A9-antisense restorer gene identified, that from pJSH1A, was transferred into a modified version of the binary vector pGA492 for use in tomato transformation. This binary vector, pBIOS222, is designed so that the selectable marker gene (pnos-nptII) can be removed after transformation. The pnos-nptII gene is cloned as a Ds element into pGA492 so that when crossed into a plant expressing Ac transposase, a proportion of the progeny lack the Ds::pnos nptII element but retain the restorer gene. The Ac transposase tomato line is constructed by transformation of tomatoes with pBIOS144 (FIG. 8a). This is a derivative of pBI 35Ac (Finnegan et al, *Plant Molecular Biology*, 22:625-633 (1993)). The A9-antisense PR-Glucanase gene was excised from pJSH1A as an XhoI, BglII fragment and cloned between the XhoI and BglII sites of pBIOS222 forming pBIOS 244 (FIG. 8b).

Tomato plants were transformed with pBIOS244 and then crossed to tomato plants expressing Ac transposase. These plants were crossed to wild-type. Progeny of this cross, containing the A9-antisense PR Glucanase gene but lacking the Ds::nptII element and transposase, were bred to homozygosity and crossed to male sterile A9-PR Glucanase tomato plants. The hybrid progeny of this cross is 100% male fertile.

EXAMPLE 5

Figure 8C:
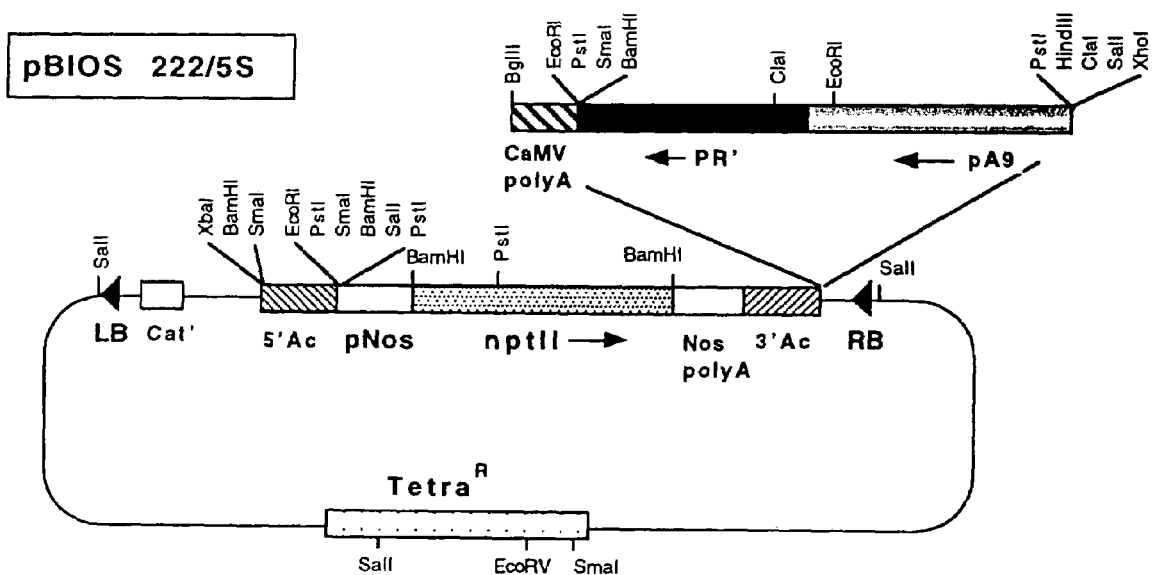

Restoration of Male Fertility to Tomato Plants Containing the A9-PR Glucanase Gene Using Partial Sense Directed Against PR-Glucanase An effective A9 partial sense restorer gene from pJSH5S was transferred into the binary vector pBIOS222 for use in tomato transformation. The A9-partial sense PR Glucanase gene was excised from pJSH5S as an XhoI, BglII fragment and cloned between the XhoI and BglII sites of pBIOS222 forming pBIOS222/5S (FIG. 8c).

Tomato plants were transformed with pBIOS222/5S and then crossed to BIOS144 tomato plants expressing Ac transposase. These plants were crossed to wild-type. Progeny of this cross, containing the A9-partial sense PR Glucanase gene but lacking the Ds::nptII element and transposase, were bred to homozygosity and crossed to male sterile A9-PR Glucanase tomato plants. The hybrid progeny of this cross is 100% male fertile.

EXAMPLE 6

Evaluation of a Male Fertility Restoration Gene in Tobacco:—A9 Promoter Anti PR-Glucanase Multimeric Ribozyme Chimaeric Gene A multimeric ribozyme (FIG. 9), consisting of 4 standard hammerhead ribozymes each with flanking arms of 10 bases, was designed specifically to cleave the PR-Glucanase mRNA at 4 distinct target sites (FIG. 5). The multimeric ribozyme gene was constructed as follows:—overlapping oligonucleotides were annealed to each other and extended by Sequenase (United States Biochemical). Adjoining bases were ligated with T4-DNA ligase. The final product was then amplified by PCR from the ligation mixture and cloned as a 198 bp EcoRI, BamHI fragment into pBluescript (SK+) digested with EcoRI and BamHI.

Sequence analysis revealed a deletion of an adenosine residue at position 15 of the catalytic sequence of ribozyme 4, preventing the in vitro activity of this ribozyme unit (FIG. 10). In vitro cleavage experiments show however that the other three ribozyme units of this multimeric ribozyme will cleave PR-glucanase message at 22° C. (FIG. 10).

The 198 bp multimeric ribozyme was cloned as a EcoRI (rendered blunt), BamHI fragment between the XbaI (rendered blunt), BamHI sites of p1415 (this is a derivative of pWP91 described in WO-A-92/11379), in which an 8 bp HindIII linker has been inserted into the EcoRV site). The resulting A9 promoter driven multimeric ribozyme gene was then cloned as a HindIII fragment into the HindIII site of the binary vector pGA-3-HyB forming p3039) (FIG. 11a). pGA-3-HyB contains a 35SCaMV-hygromycin resistance gene cloned between the SstI and EcoRI sites of pGA492.

p3039 was then transformed into a male sterile A9 PR-Glucanase tobacco line. The presence of PR-Glucanase protein in anthers was determined by Western blot analysis and the male fertility of transformants assessed. 5 plants of 38 transformants exhibited improved male fertility and lacked PR-Glucanase protein. Analysis of the progeny showed that plants containing both the A9-PR Glucanase gene and the A9-multimeric ribozyme gene lacked PR-Glucanase protein (FIG. 12).

EXAMPLE 7

Restoration of Male Fertility to Tomato Plants Containing the A9-PR Glucanase Gene Using a Multimeric Ribozyme Directed Against PR-Glucanase The A9-multimeric ribozyme gene of p3039 was excised as a HindIII fragment and cloned into the HindIII site of pBIOS222 forming pBIOS246 (FIG. 11b). Tomato plants were transformed with pBIOS246 and then crossed to tomato plants expressing transposase. These plants were crossed to wild-type. Progeny of this cross, containing the A9-multimeric ribozyme gene but lacking the Ds::nptII element and Ac transposase, were bred to homozygosity and crossed to male sterile A9-PR glucanase plants. The hybrid progeny of this cross is 100% male fertile.

The invention claimed is:

1. A transgenic tomato plant cell comprising a heterologous DNA molecule encoding a beta (1,3) PR-Glucanase enzyme operably linked to a promoter, or other regulatory sequence, which provides for expression of the DNA molecule in the tapetum and/or microsporogenous cells prior to expression of callase.

2. The transgenic tomato plant cell of claim 1, wherein the promoter is a tapetum specific promoter.

3. The transgenic tomato plant cell of claim 2, wherein the tapetum specific promoter is an A3 or A9 promoter.

4. The transgenic tomato plant cell of claim 3, wherein the tapetum specific promoter is an A9 promoter.

5. The transgenic tomato plant cell of claim 3, wherein the A3 or A9 promoter is the complete promoter.

6. The transgenic tomato plant cell of claim 3, wherein the A3 or A9 promoter is derived from *Brassicaceae*.

7. The transgenic tomato plant cell of claim 1, wherein the promoter, or other regulatory sequence, comprises one or more temporal and/or tissue control sequences of a tapetum specific promoter.

8. The transgenic tomato plant cell of claim 7, wherein the temporal and/or tissue control sequences are of an A3 or A9 promoter.

9. The transgenic tomato plant cell of claim 1, wherein the DNA molecule coding for PR-Glucanase comprises the sequence set forth in SEQ ID NO.1.

10. The transgenic tomato plant cell of claim 1, wherein the DNA molecule is a part of a vector.

11. A transgenic male sterile tomato plant comprising the tomato plant cell of any one of claims 1, 2-8, 9 or 10.

12. Propagating material derived from the transgenic male sterile tomato plant of claim 11, wherein the propagating material comprises the heterologous DNA molecule.

13. A seed from the transgenic male sterile tomato plant of claim 11, wherein the seed comprises the heterologous DNA molecule.

14. A process for producing the transgenic male sterile tomato plant of claim 11, comprising introducing into tomato plant cells the DNA molecule, so as to thereby produce the transgenic male sterile tomato plant.

* * * * *